(12) United States Patent
Friesz et al.

(10) Patent No.: US 8,658,809 B2
(45) Date of Patent: Feb. 25, 2014

(54) PROCESS FOR THE PREPARATION OF DRONEDARONE

(75) Inventors: Antal Friesz, Budapest (HU); Mariann Csatarine Nagy, Budapest (HU)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/537,930

(22) Filed: Jun. 29, 2012

(65) Prior Publication Data

US 2012/0330036 A1    Dec. 27, 2012

Related U.S. Application Data

(63) Continuation of application No. PCT/HU2010/000143, filed on Dec. 15, 2010.

(30) Foreign Application Priority Data

Jan. 8, 2010 (HU) .................. 1000010

(51) Int. Cl.
C07D 307/00 (2006.01)
A61K 31/34 (2006.01)

(52) U.S. Cl.
USPC .......................... 549/468; 514/461

(58) Field of Classification Search
CPC ............. A61K 31/34; C07D 307/00
See application file for complete search history.

(56) References Cited

U.S. PATENT DOCUMENTS

| | | | |
|---|---|---|---|
| 5,223,510 A | 6/1993 | Gubin et al. | |
| 6,828,448 B2 * | 12/2004 | Fino et al. ............... | 549/471 |
| 6,846,936 B2 | 1/2005 | Biard | |
| 6,984,741 B2 | 1/2006 | Magerlein | |
| 2012/0065411 A1 | 3/2012 | Kretzschmar et al. | |
| 2012/0077995 A1 | 3/2012 | Kretzschmar et al. | |
| 2013/0012729 A1 | 1/2013 | Bailly et al. | |
| 2013/0023677 A1 | 1/2013 | Bon et al. | |
| 2013/0023678 A1 | 1/2013 | Priem et al. | |
| 2013/0109868 A1 | 5/2013 | Friesz | |
| 2013/0131358 A1 | 5/2013 | Friesz et al. | |
| 2013/0165673 A1 | 6/2013 | Bailly et al. | |
| 2013/0165674 A1 | 6/2013 | Bailly et al. | |
| 2013/0165675 A1 | 6/2013 | Bon et al. | |

FOREIGN PATENT DOCUMENTS

| | | |
|---|---|---|
| EP | 0471609 | 2/1992 |
| EP | 1394155 | 3/2004 |
| WO | WO 96/05190 A1 | 2/1996 |
| WO | WO 02/48078 A1 | 6/2002 |
| WO | WO 02/48132 A1 | 6/2002 |
| WO | WO 03/040120 A1 | 5/2003 |
| WO | WO 03/048144 A2 | 6/2003 |
| WO | WO 2012/127173 | 9/2012 |
| WO | WO 2012/131408 | 10/2012 |
| WO | WO 2012/131409 | 10/2012 |
| WO | WO 2012/131410 | 10/2012 |

OTHER PUBLICATIONS

Sarajuddin, ATM. Salt formation to improve drug solubility. Advanced Drug Delivery. 2007, vol. 59, p. 605.*
Wamser, CC. et al. Kinetics and Mechanisms for the Two-phase Reaction between Aqueous Aniline and Benzoyl Chloride in Chloroform, with and without Pyridine Catalysis. J. Org. Chem. 1989, vol. 54, p. 150.*
U.S. Appl. No. 13/479,615, filed May 24, 2012, Friesz, et al.
International Search Report for WO2011/083346 dated Jul. 14, 2011.
U.S. Appl. No. 13/479,615—Notice of Allowance dated Mar. 6, 2013.

* cited by examiner

*Primary Examiner* — Rita Desai
*Assistant Examiner* — Ben S Michelson
(74) *Attorney, Agent, or Firm* — Scully, Scott, Murphy & Presser, P.C.

(57) ABSTRACT

The subject of the present disclosure is a novel process for the preparation of N-[2-n-butyl-3-{4-[(3-dibutylamino)propoxy]benzoyl}-1-benzofuran-5-yl]methanesulfonamide of formula I:

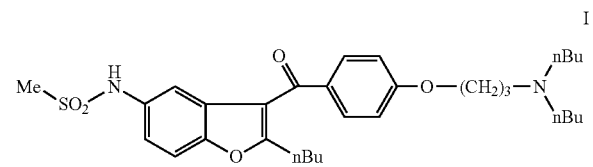

and the new intermediates of the preparation process.

13 Claims, No Drawings

PROCESS FOR THE PREPARATION OF DRONEDARONE

The present invention relates to a novel process for the preparation of N-[2-butyl-3-{4-[(3-dibutylamino)propoxy]benzoyl}-1-benzofuran-5-yl]methane-sulfonamide (dronedarone) of formula I.

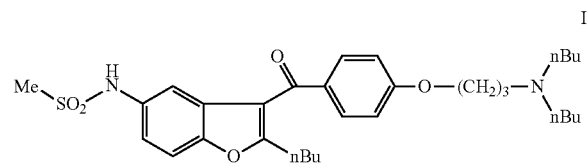

and its pharmaceutically acceptable salts, and to the new intermediates of the preparation process.

Dronedarone of formula I is used in the treatment of certain pathological changes of the cardiovascular system, especially in the treatment of angina pectoris, high blood pressure, arrhythmia and insufficient cerebral blood circulation (EP 0471609 B1).

There are several known methods for the preparation of dronedarone of formula I. Patent application of publication number WO 02/48132 discloses the following super-convergent method:

The 5-amino-2-butyl-benzofuran of formula IV

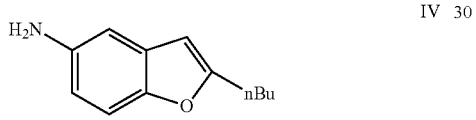

is mesylated and the resulting 2-butyl-5-methanesulfonamido-benzofuran of formula II

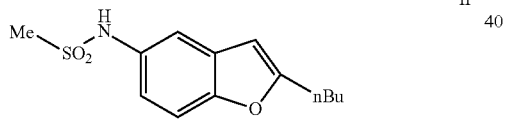

is reacted under Friedel-Crafts conditions with the 4-[3-(dibutylamino)propoxy]-benzoyl chloride hydrochloride salt of formula III

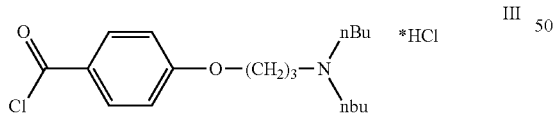

to obtain the dronedarone hydrochloride salt of formula I.

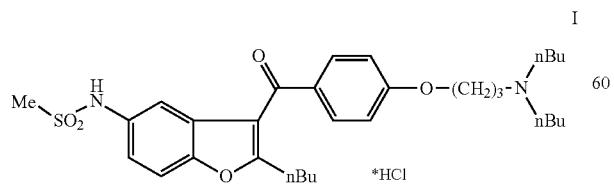

This method is very simple and economical as regards the number of the reaction steps. Its drawback is however, that in the last step the hydrochloride salt of dronedarone is obtained in a substantially contaminated form. This can be explained by the presence of the dibutylamino-propyl group in the Friedel-Crafts reaction. In the published examples the yield is 90%, during the purification steps first the raw dronedarone hydrochloride salt, then following treatment with hydrogen chloride solution in isopropanol, the purified dronedarone hydrochloride salt is obtained (90%).

Another drawback of the method is that the reactants used in the Friedel-Crafts reaction and the obtained by-products are insoluble in water, thus they cannot be removed from the system by aqueous washing.

A further drawback of the method is that during the mesylation of the 5-amino-2-butyl-benzofuran IV a double mesylated derivative always appears as a by-product of the reaction. Purification is solved by recrystallisation, its yield is 78.5%.

Our aim was to work out a novel method for the preparation of dronedarone and its pharmaceutically acceptable salts, which method avoids the above mentioned disadvantages, and is economical and industrially applicable.

We have found that if in the course of the process, instead of the 2-butyl-5-methanesulfonamido-benzofuran II, its alkali- or alkali earth metal salt is reacted with the 4-[3-(dibutylamino)propoxy]benzoyl chloride hydrochloride salt of formula III

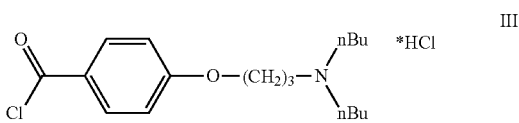

under Friedel-Crafts conditions, then the above mentioned disadvantages can be avoided.

According to our invention the 5-amino-2-butyl-benzofuran of formula IV

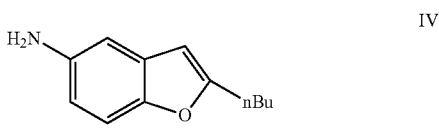

is mesylated by a method known from the literature (WO 02/48132) and
the resulting 2-butyl-5-methanesulfonamido-benzofuran of formula II

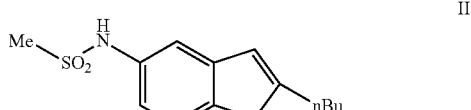

is reacted with an appropriate alkali- or alkali earth metal salt to give the respective alkali- or alkali earth metal salt of the compound of formula II,
which is then reacted as described above, with the 4-[3-(dibutylamino)propoxy]-benzoyl chloride hydrochloride salt of formula III under Friedel-Crafts conditions, to obtain the N-[2-butyl-3-{4-(3-dibutylamino)propoxy]benzoyl}-1-benzofuran-5-yl]-methanesulfonamide of formula I, which is optionally transformed into its salt, or liberated from its salt.

The advantage of the process according to the invention is that the by-product which is formed during the mesylation of the compound of formula IV will not disturb the further reaction steps, because to the obtained reaction mixture the alkali- or alkali earth metal salt solution is added, and the alkali- or alkali earth metal salt of the desired compound of formula II will dissolve and remain in the aqueous phase.

By choosing suitable reaction conditions the compound of formula I is obtained in the required purity and yield, the by-product is not formed, only a few percent of unreacted starting material may remain in the reaction mixture, which can easily be removed by aqueous washing and may be re-used.

According to one embodiment of the invention, an alkali metal salt of the compound of formula II is reacted with the compound of formula III. The term alkali metal includes lithium, sodium or potassium.

The lithium, sodium or potassium salt of the compound of formula II is prepared by reacting the 2-butyl-5-methanesulfonylamido-benzofuran of formula II with the appropriate alkali metal hydroxide (lithium hydroxide, sodium hydroxide, potassium hydroxide).

According to another embodiment of the invention, an alkali earth metal salt of the compound of formula II is reacted with the compound of formula III. The term alkali earth metal includes magnesium or calcium. The magnesium or calcium salt of the 2-butyl-5-methanesulfonylamido-benzofuran of formula II is prepared by reacting the 2-butyl-5-methanesulfonylamido-benzofuran of formula II first with an alkali metal hydroxide (lithium hydroxide or potassium hydroxide) and then with the appropriate alkali earth metal halogenide (calcium chloride, calcium bromide, magnesium chloride, magnesium bromide).

According to a preferred version of our invention, the reaction of the alkali metal or alkali earth metal salt of the compound of formula II and the compound of formula III is performed in an inert organic solvent, or in the mixture of inert organic solvents. As inert organic solvent, halogenated hydrocarbons (dichloromethane, dichloroethane, chlorobenzene) or the mixture of them can be used.

According to a preferred version of our invention, the reaction of the alkali metal or alkali earth metal salt of the compound of formula II with the compound of formula III is carried out in the presence of a Friedel-Crafts catalyst (iron (III) chloride, aluminum chloride).

According to a preferred version of our invention, the reaction of the alkali metal or alkali earth metal salt of the compound of formula II with the compound of formula III is carried out at a temperature between 10-100° C.

The 2-butyl-5-methanesulfonylamido-benzofuran of formula II

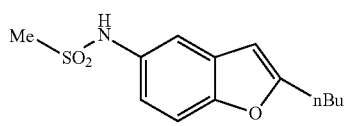

and its preparation by mesylation of the 5-amino-2-butyl-benzofuran of formula IV

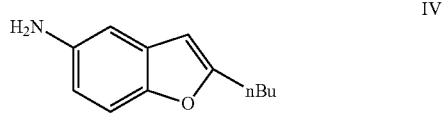

is known from the literature (WO 02/48132).

The 4-[3-(dibutylamino)propoxy]benzoyl chloride hydrochloride of formula III

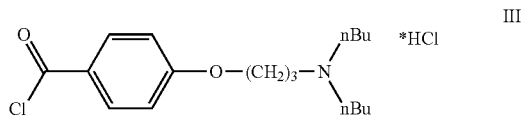

which is used in the process, and its preparation is known from the literature (WO 02/48078).

The lithium salt IIa, sodium salt IIb, potassium salt IIc, magnesium salt IId and calcium salt IIe of the compound of formula II are new compounds, not known from the literature.

Further details of the invention are demonstrated by the following examples—without limiting the claims to the examples.

EXAMPLES

Example 1

N-[2-butyl-3-{4-[(3-dibutylamino)propoxy]benzoyl}-1-benzofuran-5-yl]-methanesulfonamide I To the suspension made of 5.2 g 2-butyl-5-methanesulfonamido-benzofuran sodium salt IIb and 20 ml dichloromethane, the solution of 6.29 g 4-{3-(dibutylamino)-propoxy}benzoyl chloride hydrochloride salt III in 25 ml dichloromethane is added. The reaction mixture is stirred for 30 minutes. In 15 minutes at 5-10° C. 3.57 g iron(III) chloride is added and the reaction mixture is stirred at 20-25° C. for 2 hours. At 40° C. in 10 minutes 20 ml water is added to the mixture and the phases are separated. The dichloromethane phase is washed by stirring with 15 ml water, then with 15 ml 5% sodium hydrogen carbonate solution. The dichloromethane phase is evaporated.

9.8 g (98.0%) yellow oil is obtained.

Purity by HPLC: 98.6%

$^1$H NMR (DMSO): 0.8-0.9 ppm (m, 9H); 1.2-1.5 ppm (m, 10H); 1.67 ppm (5', 2H); 1.87 ppm (5', 2H); 2.38 ppm (t, J=7.2 Hz, 4H); 2.57 ppm (m, 2H); 2.81 ppm (t, J=7.5 Hz, 2H); 2.91 ppm (S, 3H); 9.51 ppm (t, J=6.2 Hz, 2H); 7.09 ppm (d, J=8.8 Hz, 2H); 7.24 ppm (dd, J=8.9, 2.2 Hz, 1H); 7.38 ppm (d, J=2, 1 Hz, 1H); 7.65 ppm (d, J=8.8 Hz, 1H); 7.81 ppm (d, J=8.8 Hz, 2H)

Example 2

N-[2-butyl-3-{4-[(3-dibutylamino)propoxy]benzoyl}-1-benzofuran-5-yl]-methanesulfonamide I The procedure as described in Example 1. was followed, but chlorobenzene was used, instead of dichloromethane.

Yield: 97.8%.

Purity by HPLC: 98.4%

Example 3

N-[2-butyl-3-{4-[(3-dibutylamino)propoxy]benzoyl}-1-benzofuran-5-yl]-methanesulfonamide I The procedure as described in Example 1. was followed, with the difference that instead of 2-butyl-5-methanesulfonamido-benzofuran sodium salt IIb, equivalent amount of 2-butyl-5-methanesulfonamido-benzofuran potassium salt IIc was used. The resulting material is identical with the product of Example 1.
Yield: 99.1%.
Purity by HPLC: 98.4%

Example 4

N-[2-butyl-3-{4-[(3-dibutylamino)propoxy]benzoyl}-1-benzofuran-5-yl]-methanesulfonamide I The procedure as described in Example 1. was followed, with the difference that instead of 2-butyl-5-methanesulfonamido-benzofuran sodium salt IIb, equivalent amount of 2-butyl-5-methanesulfonamido-benzofuran lithium salt IIa was used. The resulting material is identical with the product of Example 1.
Yield: 98.1%.
Purity by HPLC: 98.7%

Example 5

N-[2-butyl-3-{4-[(3-dibutylamino)propoxy]benzoyl}-1-benzofuran-5-yl]-methanesulfonamide I The procedure as described in Example 1. was followed, with the difference that instead of 2-butyl-5-methanesulfonamido-benzofuran sodium salt IIb, equivalent amount of 2-butyl-5-methanesulfonamido-benzofuran magnesium salt IIe was used. The resulting material is identical with the product of Example 1.
Yield: 97.8%.
Purity by HPLC: 99.0%

Example 6

N-[2-butyl-3-{4-[(3-dibutylamino)propoxy]benzoyl}-1-benzofuran-5-yl]-methanesulfonamide I The procedure as described in Example 1. was followed, with the difference that instead of 2-butyl-5-methanesulfonamido-benzofuran sodium salt IIb, equivalent amount of 2-butyl-5-methanesulfonamido-benzofuran calcium salt IId was used. The resulting material is identical with the product of Example 1.
Yield: 97.7%.
purity by HPLC: 97.6%

Example 7

N-[2-butyl-3-{4-[(3-dibutylamino)propoxy]benzoyl}-1-benzofuran-5-yl]-methanesulfonamide I The procedure as described in Example 1. was followed, but 2.93 g aluminum chloride was used, instead of iron(III) chloride.
The resulting material is identical with the product of Example 1.
Yield: 89.9%.
Purity by HPLC: 96.1%

Example 8

2-butyl-5-methanesulfonamido-benzofuran lithium salt IIa 2.23 g 2-butyl-5-methanesulfonamido-benzofuran II is added under stirring to the solution of 0.20 g lithium hydroxide in 5 ml water. The reaction mixture is stirred at room temperature for 1 hour and then kept at 0-5° C. for 8 hours. The precipitated white material was collected, washed with 1 ml 5° C. water and dried at 70° C.
Mass of the product: 1.7 g (74.5%)
Melting point: 252.1-253.7° C.
Elemental analysis: C, 51.98%; H, 5.79%; N, 4.61%; S, 10.44%; Li, 2.41%.
(Calculated values: C, 57.1%; H, 5.86%; N, 5.13%; S, 11.7%; Li, 2.56%).

Example 9

2-butyl-5-methanesulfonamido-benzofuran sodium salt IIb 2.12 g 2-butyl-5-methanesulfonamido-benzofuran II was added to the solution of 1 g sodium hydroxide in 75 ml water. The resulting suspension was warmed to 70° C., then allowed to cool to 20° C. and stirred at 5-10° C. for 1 hour. The product was filtered off, dried in vacuum.
Mass of the product: 2.04 g (89.0%)
Melting point: 226.3-228.9° C.
Elemental analysis: C, 59.9%; H, 5.63%; N, 5.16%; S, 11.14%; Na, 7.2%.
(Calculated values: C, 59.98%; H, 5.54%; N, 4.84%; S, 11.07%; Na, 7.94%).

Example 10

2-butyl-5-methanesulfonamido-benzofuran sodium salt IIb

The procedure as described in Example 9. was followed, but 40 ml water was used in the reaction. The resulting material is identical with the product of Example 9.
Yield: 95.0%.

Example 11

2-butyl-5-methanesulfonamido-benzofuran potassium salt IIc 2.12 g 2-butyl-5-methanesulfonamido-benzofuran II was added to the solution of 1 g of 85% potassium hydroxide in 25 ml water. The reaction mixture was stirred at room temperature for 1 hour, and then at 5° C. for 2 hours. The product was filtered off, dried in vacuum.
Mass of the product: 2.0 g (82.0%)
Melting point: 103.2-105.7° C.
Elemental analysis: C, 50.37%; H, 5.16%; N, 4.54%; S, 9.53%; K, 12.0%.
(Calculated values: C, 51.07%; H, 5.24%; N, 4.58%; S, 10.47%; K, 12.8%).

Example 12

2-butyl-5-methanesulfonamido-benzofuran potassium salt IIc

The procedure as described in Example 11. was followed, but 10 ml water was used in the reaction. The resulting material is identical with the product of Example 11.
Yield: 94.0%.

Example 13

2-butyl-5-methanesulfonamido-benzofuran calcium salt IIe 2.0 g 2-butyl-5-methanesulfonamido-benzofuran II was added to the solution of 0.5 g 85% potassium hydroxide in 20 ml water. The reaction mixture was stirred for 30 minutes. To the obtained solution 0.89 g calcium chloride dissolved in 5 ml water was added in 10 minutes, the resulting suspension was stirred at 20-25° C. for 1 hour and then at 5° C. for 2 hours. The product was filtered off and dried.
Mass of the product: 1.8 g (86.1%)
Melting point: 103.4-105.7° C.
Elemental analysis: C, 51.74%; H, 5.50%; N, 4.55%; S, 10.29%; Ca, 5.8%.
(Calculated values: C, 54.47%; H, 5.58%; N, 4.89%; S, 11.17%; Ca, 6.99%).

Example 14

2-butyl-5-methanesulfonamido-benzofuran calcium salt IIe

The procedure as described in Example 13. was followed, but 15 ml water was used in the reaction, instead of 20 ml. The resulting material is identical with the product of Example 13.
Yield: 92.0%.

Example 15

2-butyl-5-methanesulfonamido-benzofuran magnesium salt IId 1.6 g 2-butyl-5-methanesulfonamido-benzofuran II was added to the solution of 0.28 g 85% potassium hydroxide in 16 ml water. The reaction mixture was stirred for 30 minutes. To the obtained solution 0.76 g magnesium chloride dissolved in 5 ml water was added in 10 minutes, the resulting suspension was stirred at 20-25° C. for 1 hour and then at 5° C. for 2 hours. The product was filtered off and dried.
Yield: 1.4 g (83.8%)
Melting point: above 270° C.
Elemental analysis: C, 51.74%; H, 5.50%; N, 4.55%; S, 10.29%; Mg, 4.8%.
(Calculated values: C, 56.0%; H, 5.74%; N, 5.03%; S, 11.49; Mg, 4.36%).

Example 16

2-butyl-5-methanesulfonamido-benzofuran magnesium salt IId

The procedure as described in Example 15. was followed, but 10 ml water was used in the reaction, instead of 16 ml. The resulting material is identical with the product of Example 15.
Yield: 93.7%

What is claimed is:

1. A process for the preparation of N-[2-butyl-3-{4-[(3-dibutylamino)propoxy]-benzoyl}-1-benzofuran-5-yl]methanesulfonamide of formula I:

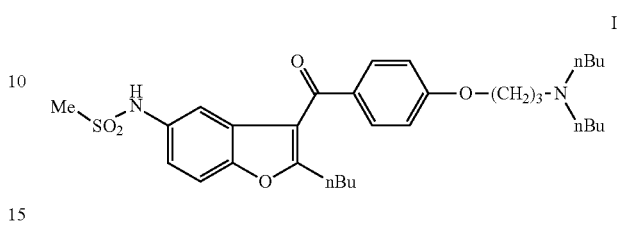

or a pharmaceutically acceptable salt thereof, comprising reacting an alkali- or alkali earth metal salt of the compound of formula II:

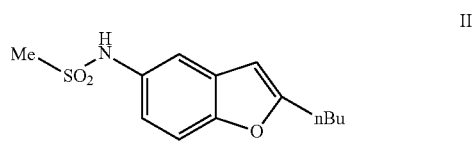

with the 4-[3-(dibutylamino)propoxy]benzoyl chloride hydrochloride of formula III

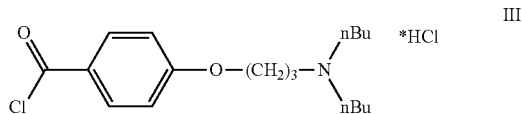

in the presence of a catalyst, and optionally, transforming the compound of formula I into a salt thereof, or liberating the compound of formula I from a salt thereof.

2. The process according to claim 1, wherein the alkali metal is selected from lithium, sodium and potassium, and the alkali earth metal is selected from magnesium and calcium.

3. The process according to claim 1, further comprising carrying out the reaction of the compound of formula II and the compound of formula III in an inert solvent or in a mixture of invert solvents.

4. The process according to claim 3, wherein the inert solvent is a halogenated hydrocarbon.

5. The process according to claim 4, wherein the halogenated hydrocarbon is selected from the group consisting of dichloromethane, dichloroethane, chlorobenzene and a mixture thereof.

6. The process according to claim 1, wherein the catalyst is selected from iron(III) chloride and aluminum chloride.

7. The process as defined in claim 1, further comprising carrying out the reaction at a temperature between 10-100° C.

8. A compound which is an alkali metal- and alkali earth metal salt of the 2-butyl-5-methanesulfonamido-benzofuran of formula II:

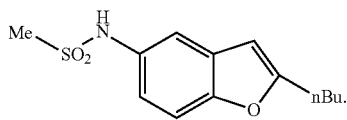

9. The compound according to claim 8, selected from the group consisting of the lithium salt IIa, sodium salt IIb, potassium salt IIc, magnesium salt IId and calcium salt IIe of the compound of formula II.

10. A process for preparing the compound according to claim 8, comprising reacting the compound of formula II:

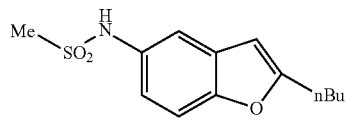

with the appropriate alkali metal hydroxide.

11. The process according to claim 10, wherein the alkali metal hydroxide is selected from the group consisting of lithium hydroxide, sodium hydroxide and potassium hydroxide.

12. A process for preparing the compound according to claim 8, comprising reacting the compound of formula II

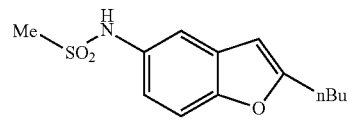

with lithium hydroxide or potassium hydroxide, and then reacting with the appropriate alkali earth metal halogenide.

13. The process according to claim 12, wherein the alkali earth metal halogenide is selected from the group consisting of magnesium chloride, magnesium bromide, calcium chloride and calcium bromide.

* * * * *